US009981946B2

(12) United States Patent
Gong et al.

(10) Patent No.: US 9,981,946 B2
(45) Date of Patent: *May 29, 2018

(54) PYRIDINE-SUBSTITUTED 2-AMINOPYRIDINE PROTEIN KINASE INHIBITORS

(71) Applicants: CHIA TAI TIANQING PHARMACEUTICAL GROUP CO., LTD, Lianyungang, Jiangsu (CN); LIANYUNGANG RUNZHONG PHARMACEUTICAL CO., LTD., Lianyungang, Jiangsu Province (CN); CENTAURUS BIOPHARMA CO., LTD., Beijing (CN)

(72) Inventors: Feng Gong, Lianyungang (CN); Xinlu Li, Lianyungang (CN); Rui Zhao, Lianyungang (CN); Xiquan Zhang, Lianyungang (CN); Xinhe Xu, Beijing (CN); Xijie Liu, Beijing (CN); Dengming Xiao, Beijing (CN); Yongxin Han, Beijing (CN)

(73) Assignees: CHIA TAI TIANQING PHARMACEUTICAL GROUP CO., LTD., Lianyungang (CN); LAINYUNGANG RUNZHONG PHARMACEUTICAL CO., LTD., Lianyungang (CN); CENTAURUS BIOPHARMA CO., LTD., Haidian District (CN)

(*) Notice: Subject to any disclaimer, the term of this patent is extended or adjusted under 35 U.S.C. 154(b) by 0 days. days.

This patent is subject to a terminal disclaimer.

(21) Appl. No.: 15/329,046

(22) PCT Filed: Jul. 31, 2015

(86) PCT No.: PCT/CN2015/085727
§ 371 (c)(1),
(2) Date: Jan. 25, 2017

(87) PCT Pub. No.: WO2016/015676
PCT Pub. Date: Feb. 4, 2016

(65) Prior Publication Data
US 2017/0226084 A1 Aug. 10, 2017

(30) Foreign Application Priority Data
Jul. 31, 2014 (CN) .......................... 2014 1 0371344

(51) Int. Cl.
*C07D 401/14* (2006.01)
*A61K 31/506* (2006.01)
(52) U.S. Cl.
CPC ................. *C07D 401/14* (2013.01)
(58) Field of Classification Search
CPC .................................................. C07D 401/14
See application file for complete search history.

(56) References Cited

U.S. PATENT DOCUMENTS

| 9,708,295 | B2* | 7/2017 | Xiao .................. C07D 401/14 |
| 2006/0046991 | A1 | 3/2006 | Cui et al. |
| 2006/0178374 | A1 | 8/2006 | Cui et al. |
| 2009/0197862 | A1 | 8/2009 | Steinig et al. |
| 2016/0002205 | A1 | 1/2016 | Xiao et al. |

FOREIGN PATENT DOCUMENTS

| CN | 102718745 A | 10/2012 |
| CN | 103965168 A | 8/2014 |
| CN | 104650049 A | 5/2015 |
| JP | 2008/510790 A | 4/2008 |
| JP | 2008/510792 A | 4/2008 |
| JP | 2011/511005 A | 4/2011 |
| KR | 10-2007-0038562 A | 4/2007 |
| WO | WO 2006/021884 A2 | 3/2006 |
| WO | WO 2006/021886 A1 | 3/2006 |
| WO | WO 2009/099982 A1 | 8/2009 |
| WO | WO 2011/138751 A2 | 11/2011 |
| WO | WO 2012/116050 A2 | 8/2012 |
| WO | WO 2014/117718 A1 | 8/2014 |

OTHER PUBLICATIONS

Golub, T. R., "Molecular classification of cancer: class discovery and class prediction by gene expression monitoring." Science (1999), vol. 286, 531-537. (Year: 1999).*
Lala, P. K., "Role or nitric oxide is tumor progression: Lessons from experimental tumors." Cancer and Metastasis Reviews (1998), 17(1), 91-106. (Year: 1998).*
Jaworska, J., "Review of methods for assessing the applicability domains of SARs and QSARs." Alternatives to Laboratory Animals 33 (2005): 445-459. (Year: 2005).*
Voskoglou-Nomikos T.,"Clinical predictive value of the in vitro cell line, human xenograft, and mouse allograft preclinical cancer models." (2003) Clinical Cancer Research, vol. 9, 4227-4239. (Year: 2003).*
Saal, C., "Pharmaceutical salts: a summary on doses of salt formers from the Orange Book." European Journal of Pharmaceutical Sciences 49.4 (2013): 614-623.*
Roskoski, R.,"Anaplastic lymphoma kinase (ALK): structure, oncogenic activation, and pharmacological inhibition." Pharmacological research 68.1 (2013): 68-94.*
International Bureau, International Search Report in International Patent Application No. PCT/CN2015/085727, dated Oct. 23, 2015.
Cui et al., "Structure Based Drug Design of Crizotinib (PF-02341066), a Potent and Selective Dual Inhibitor of Mesenchymal-Epithelial Transition Factor (c-MET) Kinase and Anaplastic Lymphoma Kinase (ALK)," *J. Med. Chem.*, 54: 6342-6363 (2011).

(Continued)

*Primary Examiner* — John M Mauro
(74) *Attorney, Agent, or Firm* — Leydig, Voit & Mayer

(57) ABSTRACT

The present invention discloses pharmaceutically acceptable acid salts of pyridine-substituted 2-aminopyridine derivatives as protein kinase inhibitors, preparation methods, pharmaceutical compositions thereof, and use thereof for the treatment of diseases associated with protein kinase.

20 Claims, No Drawings

(56) References Cited

OTHER PUBLICATIONS

Huang et al., "Design of Potent and Selective Inhibitors to Overcome Clinical Anaplastic Lymphoma Kinase Mutations Resistant to Crizotinib," *J. Med. Chem.*, 57: 1170-1187 (2014).
International Search Report for International Application No. PCT/CN2014/071595 dated May 19, 2014.
Kruczynski et al., "Anaplastic Lymphoma Kinase as a Therapeutic Target," *Expert Opin. Ther. Targets*, 16(11): 1127-1138 (2012).
Milkiewicz et al., "Inhibitors of anaplastic lymphoma kinase: a patent review," *Expert Opin. Ther. Patents*, 20(12): 1653-1681 (2010).
Rodig et al., "Crizotinib, a small-molecule dual inhibitor of the c-Met and ALK receptor tyrosine kinases," *Curr Opin Investig Drugs*, 11(12): 1477-1490 (2010).

* cited by examiner

PYRIDINE-SUBSTITUTED 2-AMINOPYRIDINE PROTEIN KINASE INHIBITORS

CROSS-REFERENCE TO RELATED APPLICATIONS

This patent application is the U.S. National Stage of International Patent Application No. PCT/CN2015/085727, filed Jul. 31, 2015, which claims the benefit of Chinese Patent Application No. 201410371344.3, filed Jul. 31, 2014, which are each incorporated herein by reference.

TECHNICAL FIELD

The present invention belongs to the field of medicinal chemistry, specifically pertains to pharmaceutically acceptable acid salts of pyridine-substituted 2-aminopyridine derivatives.

BACKGROUND

Recent molecular biology studies indicate that tyrosine kinase (Protein Tyrosine Kinases, PTKs) cell signal transduction pathway plays an extremely important role in tumor formation and development. Inhibition of tyrosine kinase activity, can reduce the activation of intracellular signal transduction pathways, thereby inhibiting tumor cell induced survival and proliferation, and achieving tumor therapeutic effect.

Anaplastic lymphoma kinase (ALK), as a receptor tyrosine kinase, is a member of the insulin receptor superfamily and plays an important role in tumor cell growth and development. ALK gene can fuse with a variety of protein genes, be expressed to produce ALK protein, and can also generate variations such as mutation, amplification, and the like. In 1997, the oncogenic ALK gene rearrangement on the short arm of chromosome 2 of allobiosis large cell lymphoma was originally described, whereafter it was also found in other malignancies including diffuse large B-cell lymphoma and malignant tissues ball histiocytosis, as well as a variety of solid tumors including inflammatory fibroblastoma, esophageal squamous cell carcinoma, neuroblastoma along with non-small cell lung carcinoma (NSCLC) recently reported.

In 2007, it was originally reported that ALK gene may encode and produce ALK by fusing with EML4 gene to form fusion gene, and thereby promote the growth of lung cancer cells. EML4-ALK fusion is caused by the insertion of the short arm of chromosome 2, and many types of variations have been found to date. Test shows that all of the fusion genes have biological functions, and the product they express is a chimeric tyrosine kinase, which began to be reported gradually in the study associated with NSCLC since 2007.

Because of the discovery of EML4-ALK fusion gene and the unique effect of the ALK inhibitor in the subgroup population thereof, NSCLC can be divided into different subtypes such as EGFR mutation, KRAS mutation, EML4-ALK gene fusion type, and the like, according to different molecular pathogenesis. In general NSCLC patients, the positive rate of EML4-ALK fusion gene is low in a range of between 3% to 7%. EML4-ALK fusion gene mainly presents in non-smoking lung adenocarcinoma patients, and is mutually repulsive with both EGFR mutation and KRAS mutation. A study in 2010 showed that EML4-ALK fusion gene positive rate was 16.13% in Chinese lung adenocarcinoma patients, significantly higher than that of European and American patients; the positive rate was 19.23% in non-smoking lung adenocarcinoma patients; the mutation rate thereof was up to 42.8% in lung adenocarcinoma patients without EGFR and KRAS mutations.

Although a large amount of compounds with protein kinase inhibitory activity have been studied, and some protein kinase inhibitors have been launched for the antitumor therapy, drug resistance may arise. Therefore, it is urgent to develop new protein kinase inhibitors, such as ALK kinase inhibitors, for the prevention, mitigation and/or treatment of cancers mediated by protein kinases (such as ALK), such as ALK-positive non-small cell lung carcinoma (NSCLC) and the like.

SUMMARY

In one aspect, the present application provides a pharmaceutically acceptable acid salt of 5-((R)-1-(2,6-dichloro-3-fluorophenyl)ethoxy)-4'-methoxy-6'-((S)-2-methyl piperazin-1-yl)-3,3'-bipyridin-6-amine (having the following structure of formula I, hereinafter referred to as a compound of formula I).

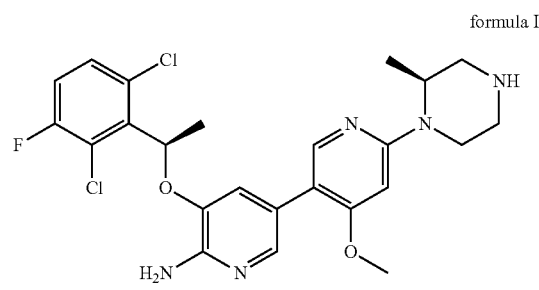 [SMILES: COc1cc(N2CCNC[C@@H]2C)ncc1-c1cnc(N)c(O[C@H](C)c2c(Cl)ccc(F)c2Cl)c1]

formula I

In another aspect, the present application provides a method for preparing a pharmaceutically acceptable acid salt of a compound of formula I, wherein the method comprises reacting the compound of formula I with the pharmaceutically acceptable acid.

In another aspect, the application provides a pharmaceutical composition comprising a therapeutically effective amount of a pharmaceutically acceptable acid salt of a compound of formula I, and a pharmaceutically acceptable carrier, excipient or diluent.

In another aspect, the application provides use of a pharmaceutically acceptable acid salt of a compound of formula I, or the pharmaceutical composition thereof for the manufacture of a medicament for the treatment and/or prophylaxis of diseases associated with protein kinases.

In still another aspect, the present application provides a method for the treatment and/or prophylaxis of diseases associated with protein kinases, wherein the method comprises administering to a mammal in need, preferably a human, a pharmaceutically acceptable acid salt of a compound of formula I, or a pharmaceutical composition thereof.

In still another aspect, the present application provides a pharmaceutically acceptable acid salt of a compound of formula I, or a pharmaceutical composition thereof for use in a method for the treatment and/or prophylaxis of diseases associated with protein kinases.

DETAILED DESCRIPTION OF INVENTION

The following description includes specific details to provide a thorough understanding of various disclosed embodiments. However, the relevant person skilled in the art will recognize that, use other methods, components, materials and the like instead of one or more of these specific details disclosed herein can achieve the embodiments.

Unless otherwise required by the present application, throughout the specification and the subsequent claims, the word "include (comprise)" and its English variants such as "includes (comprises)" and "including (comprising)" shall be construed as open-ended and inclusive meaning, that is, "including but not limited to".

Throughout this specification the phrase "one embodiment" or "an embodiment" or "in another embodiment" or "in some embodiments" means at least one embodiment includes particular reference element, structure, or characteristic relevant to the embodiment. Thus, the phrase which appears in different locations throughout the specification, "in one embodiment" or "in an embodiment" or "in another embodiment" or "in some embodiments" is not necessarily all referring to the same embodiment. Furthermore, the particular element, structures, or characteristics may be optionally combined in any suitable manner in one or more embodiments.

It should be understood that the singular form of the articles "a" used in this specification and the appended claims (corresponding to the English "a", "an" and "the") includes plural object, unless the context clearly rules. Thus, for example, reaction including the "catalyst" mentioned includes a catalyst, or two or more catalysts. It should also be understood that the term "or" generally includes "and/or" meaning and then used, unless the context clearly defined.

In one aspect, the present application provides a pharmaceutically acceptable acid salt of 5-((R)-1-(2,6-dichloro-3-fluorophenyl)ethoxy)-4'-methoxy-6'-((S)-2-methylpiperazin-1-yl)-3,3'-bipyridin-6-amine (having the structure of formula I, herein after referred to as a compound of formula I).

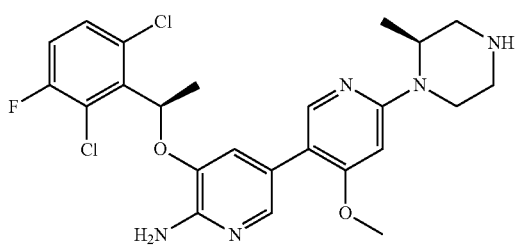

formula I

In certain embodiments, wherein the pharmaceutically acceptable acid includes inorganic and organic acids. Wherein, examples of the inorganic acids include, but are not limited to, sulfuric acid, carbonic acid, nitric acid, hydrochloric acid, hydrobromic acid, hydroiodic acid, phosphoric acid and metaphosphoric acid; organic acids include aliphatic and aromatic organic acids, examples of which include, but are not limited to, trifluoroacetic acid, lactic acid, fumaric acid, mandelic acid, glycolic acid, toluene sulfonic acid (such as p-toluenesulfonic acid, o-toluenesulfonic acid), citric acid, methanesulfonic acid, formic acid, acetic acid, benzoic acid, phenylacetic acid, malonic acid, cinnamic acid, malic acid, maleic acid, tartaric acid, oxalic acid, acrylic acid, crotonic acid, oleic acid and linoleic acid. In some preferred embodiments, the pharmaceutically acceptable acid selected from sulfuric acid, hydrochloric acid, phosphoric acid, p-toluenesulfonic acid, citric acid, methanesulfonic acid, malic acid, maleic acid, tartaric acid and fumaric acid.

In the preparation of a pharmaceutically acceptable acid salt of a compound of formula I, the pharmaceutically acceptable acid may be at an equal molar ratio (the molar ratio of a compound of formula I to the acid is 1:1) or a different molar ratio for the preparation of the salt, which depends on the acid which is a monobasic acid or polybasic acid, and the desired salt. For example, in the salt, the molar ratio of a compound of formula I to the pharmaceutically acceptable acid is 1:0.5-4 or 1:1-3. In some embodiments, the molar ratio of a compound of formula I to the pharmaceutically acceptable acid is 1:0.5, 1:1, 1:1.5, 1:2, 1:2.5, 1:3, 1:3.5 or 1:4.

In some embodiments, a pharmaceutically acceptable acid salt of a compound of formula I provided herein is selected from the following salts:

(1) 5-((R)-1-(2,6-dichloro-3-fluorophenyl)ethoxy)-4'-methoxy-6'-((S)-2-methyl piperazin-1-yl)-3,3'-bipyridin-6-amine hydrochloride; in some embodiments, the molar ratio of the compound of formula I to hydrochloric acid is 1:0.5, 1:1, 1:1.5, 1:2, 1:2.5, 1:3, 1:3.5 or 1:4; in one embodiment, the molar ratio of the compound of formula I to hydrochloric acid is 1:0.5; in one embodiment, the molar ratio of the compound of formula I to hydrochloric acid is 1:1; in one embodiment, the molar ratio of a compound of formula I to hydrochloric acid is 1:1.5; in one embodiment, the molar ratio of the compound of formula I to hydrochloric acid is 1:2; in one embodiment, the molar ratio of the compound of formula I to hydrochloric acid is 1:2.5; in one embodiment, the molar ratio of the compound of formula I to hydrochloric acid is 1:3.

(2) 5-((R)-1-(2,6-dichloro-3-fluorophenyl)ethoxy)-4'-methoxy-6'-((S)-2-methyl piperazin-1-yl)-3,3'-bipyridin-6-amine sulfate; in some embodiments, the molar ratio of the compound of formula I to sulfuric acid is 1:0.5, 1:1, 1:1.5, 1:2, 1:2.5, 1:3, 1:3.5 or 1:4; in one embodiment, the molar ratio of the compound of formula I to sulfuric acid is 1:0.5; in one embodiment, the molar ratio of the compound of formula I to sulfuric acid is 1:1; in one embodiment, the molar ratio of the compound of formula I to sulfuric acid is 1:1.5; in one embodiment, the molar ratio of the compound of formula I to sulfuric acid is 1:2; in one embodiment, the molar ratio of the compound of formula I to sulfuric acid is 1:2.5; in one embodiment, the molar ratio of the compound of formula I to sulfuric acid is 1:3.

(3) 5-((R)-1-(2,6-dichloro-3-fluorophenyl)ethoxy)-4'-methoxy-6'-((S)-2-methyl piperazin-1-yl)-3,3'-bipyridin-6-amine citrate; in some embodiments, the molar ratio of the compound of formula I to citric acid is 1:0.5, 1:1, 1:1.5, 1:2, 1:2.5, 1:3, 1:3.5 or 1:4; in one embodiment, the molar ratio of the compound of formula I to citric acid is 1:0.5; in one embodiment, the molar ratio of the compound of formula I to citric acid is 1:1; in one embodiment, the molar ratio of the compound of formula I to citric acid is 1:1.5; in one embodiment, the molar ratio of the compound of formula I to citric acid is 1:2; in one embodiment, the molar ratio of the compound of formula I to citric acid is 1:2.5; in one embodiment, the molar ratio of the compound of formula I to citric acid is 1:3.

(4) 5-((R)-1-(2,6-dichloro-3-fluorophenyl)ethoxy)-4'-methoxy-6'-((S)-2-methyl piperazin-1-yl)-3,3'-bipyridin-6-amine malate; in some embodiments, the molar ratio of the compound of formula I to malic acid is 1:0.5, 1:1, 1:1.5, 1:2, 1:2.5, 1:3, 1:3.5 or 1:4; in one embodiment, the molar ratio of the compound of formula I to malic acid is 1:0.5; in one embodiment, the molar ratio of the compound of formula I to malic acid is 1:1; in one embodiment, the molar ratio of the compound of formula I to malic acid is 1:1.5; in one embodiment, the molar ratio of the compound of formula I to malic acid is 1:2; in one embodiment, the molar ratio of the compound of formula I to malic acid is 1:2.5; in one embodiment, the molar ratio of the compound of formula I to malic acid is 1:3.

(5) 5-((R)-1-(2,6-dichloro-3-fluorophenyl)ethoxy)-4'-methoxy-6'-((S)-2-methyl piperazin-1-yl)-3,3'-bipyridin-6-amine maleate; in some embodiments, the molar ratio of the compound of formula I to maleic acid is 1:0.5, 1:1, 1:1.5, 1:2, 1:2.5, 1:3, 1:3.5 or 1:4; in one embodiment, the molar ratio of the compound of formula I to maleic acid is 1:0.5; in one embodiment, the molar ratio of the compound of formula I to maleic acid is 1:1; in one embodiment, the molar ratio of the compound of formula I to maleic acid is 1:1.5; in one embodiment, the molar ratio of the compound of formula I to maleic acid is 1:2; in one embodiment, the molar ratio of the compound of formula I to maleic acid is 1:2.5; in one embodiment, the molar ratio of the compound of formula I to maleic acid is 1:3.

(6) 5-((R)-1-(2,6-dichloro-3-fluorophenyl)ethoxy)-4'-methoxy-6'-((S)-2-methyl piperazin-1-yl)-3,3'-bipyridin-6-amine tartrate; in some embodiments, the molar ratio of the compound of formula I to tartaric acid is 1:0.5, 1:1, 1:1.5, 1:2, 1:2.5, 1:3, 1:3.5 or 1:4; in one embodiment, the molar ratio of the compound of formula I to tartaric acid is 1:0.5; in one embodiment, the molar ratio of the compound of formula I to tartaric acid is 1:1; in one embodiment, the molar ratio of the compound of formula I to tartaric acid is 1:1.5; in one embodiment, the molar ratio of the compound of formula I to tartaric acid is 1:2; in one embodiment, the molar ratio of the compound of formula I to tartaric acid is 1:2.5; in one embodiment, the molar ratio of the compound of formula I to tartaric acid is 1:3.

(7) 5-((R)-1-(2,6-dichloro-3-fluorophenyl)ethoxy)-4'-methoxy-6'-((S)-2-methyl piperazin-1-yl)-3,3'-bipyridin-6-amine fumarate; in some embodiments, the molar ratio of the compound of formula I to fumaric acid is 1:0.5, 1:1, 1:1.5, 1:2, 1:2.5, 1:3, 1:3.5 or 1:4; in one embodiment, the molar ratio of the compound of formula I to fumaric acid is 1:0.5; in one embodiment, the molar ratio of the compound of formula I to fumaric acid is 1:1; in one embodiment, the molar ratio of the compound of formula I to fumaric acid is 1:1.5; in one embodiment, the molar ratio of the compound of formula I to fumaric acid is 1:2; in one embodiment, the molar ratio of the compound of formula I to fumaric acid is 1:2.5; in one embodiment, the molar ratio of the compound of formula I to fumaric acid is 1:3.

In another aspect, the present application provides a method for preparing a pharmaceutically acceptable acid salt of 5-((R)-1-(2,6-dichloro-3-fluorophenyl)ethoxy)-4'-methoxy-6'-((S)-2-methylpiperazin-1-yl)-3,3'-bipyridin-6-amine, wherein the method comprises reacting 5-((R)-1-(2,6-dichloro-3-fluorophenyl)ethoxy)-4'-methoxy-6'-((S)-2-methylpiperazin-1-yl)-3,3'-bipyridin-6-amine (having the structure of formula I, hereinafter referred to as a compound of formula I) with the pharmaceutically acceptable acid.

In certain embodiments, wherein the pharmaceutically acceptable acids include inorganic and organic acids. Examples of the inorganic acids include, but are not limited to, sulfuric acid, carbonic acid, nitric acid, hydrochloric acid, hydrobromic acid, hydroiodic acid, phosphoric acid and metaphosphoric acid. The organic acids include aliphatic acids and aromatic acids, examples of which include but are not limited to, trifluoroacetic acid, lactic acid, fumaric acid, mandelic acid, glycolic acid, toluene sulfonic acid (such as p-toluenesulfonic acid, o-toluenesulfonic acid), citric acid, methanesulfonic acid, formic acid, acetic acid, benzoic acid, phenylacetic acid, malonic acid, cinnamic acid, malic acid, maleic acid, tartaric acid, oxalic acid, acrylic acid, crotonic acid, oleic acid and linoleic acid. In some preferred embodiments, the pharmaceutically acceptable acid is selected from sulfuric acid, hydrochloric acid, phosphoric acid, p-toluenesulfonic acid, citric acid, methanesulfonic acid, malic acid, maleic acid, tartaric acid and fumaric acid.

In certain embodiments of the preparation of the pharmaceutically acceptable acid salt of the compound of formula I, the salt may be prepared by the reaction of the compound of formula I dissolved in a suitable single solvent or mixed solvents containing the corresponding acid, or the salt may be obtained by the reaction that the compound of formula I is dissolved in a suitable single solvent or mixed solvents followed by adding the corresponding acid.

In certain embodiments of the preparation of a pharmaceutically acceptable acid salt of a compound of formula I, the pharmaceutically acceptable acid may be reacted with the compound of formula I in an equal molar ratio (the molar ratio of the compound of formula I to the acid is 1:1) or a different molar ratio, which depends on the acid which is a monobasic acid or polybasic acid, and the desired salt. For example, in the preparation of the salt, the molar ratio of the compound of formula I to the acid is 1:0.5-4 or 1:1-3.

The pharmaceutically acceptable acid salt of the compound of formula I can also be prepared by adjusting the amount of the pharmaceutically acceptable acid, for example, relative to the amount of the compound of formula I, stoichiometric amount or excess amount of the pharmaceutically acceptable acid is used. In certain embodiments of the preparation of the salt, the molar ratio of the compound of formula I to the pharmaceutically acceptable acid is 1:0.5, 1:1, 1:1.5, 1:2, 1:2.5, 1:3, 1:3.5 or 1:4.

In certain embodiments of the preparation of the pharmaceutically acceptable acid salt of the compound of formula I, the reaction temperature is 0° C. to the boiling point of the solvent system, preferably 0° C.-50° C., more preferably 0° C.-35° C.

In certain embodiments of the preparation of the pharmaceutically acceptable acid salt of the compound of formula I, the reaction is carried out under the protection of an inert gas such as nitrogen. In certain embodiments, the reaction time is 0.5-5 h.

In certain embodiments, suitable solvents include ethers, alcohols, ketones, nitriles, esters, hydrocarbons, halogenated hydrocarbons, and any combination thereof. Examples of the solvents include, but are not limited to, tetrahydrofuran, dioxane, diisopropyl ether, diethyl ether, methanol, ethanol, isopropanol, acetone, acetonitrile, ethyl acetate, ethyl formate, hexane, methylene chloride, chloroform and any combination thereof.

In another aspect, the present application provides a pharmaceutical composition comprising a therapeutically effective amount of a pharmaceutically acceptable acid salt of a compound of formula I, and a pharmaceutically acceptable carrier, excipient or diluent.

"Pharmaceutically acceptable carrier and excipient" refers to an inert substance beneficial to the administration of active ingredient, including, but not limited to, any glidants, sweetening agents, diluents, preservatives, dyes/colorants, flavor enhancers, surfactants, wetting agents, dispersing agents, disintegrating agents, suspending agents, stabilizers, isotonic agents, solvents, and emulsifiers, which are licensed by the State Food and Drug Administration and acceptable for human or animals (such as livestock). Non-limiting examples of the carriers and excipients include calcium carbonate, calcium phosphate, various sugars and various types of starch, cellulose derivatives, gelatin, vegetable oil, and polyethylene glycol.

The pharmaceutical compositions of the present invention may be formulated into solid, semi-solid, liquid or gaseous formulations, such as tablets, pills, capsules, powders, granules, pastes, emulsions, suspensions, solutions, suppositories, injections, inhalants, gels, microspheres, and aerosols, and the like.

Typical administration routes of the pharmaceutical composition of the present invention, include, but are not limited to, oral, rectal, transmucosal, enteral administration, or topical, transdermal, inhaled, parenteral, sublingual, intravaginal, intranasal, intraocular, intraperitoneal, intramuscular, subcutaneous, and intravenous administration. Oral administration is preferred.

In another aspect, the present application provides a method to regulate the protein kinase activity, which comprises contacting the protein kinase with a pharmaceutically acceptable acid salt of a compound of formula I. Preferably, the protein kinase is selected from ALK. In addition, the protein kinases comprise mutated kinases, wherein the mutated kinases are selected from mutated ALK kinase.

In another aspect, the present application provides a use of a pharmaceutically acceptable acid salt of a compound of formula I, or a pharmaceutical composition thereof for the manufacture of a medicament for the treatment and/or prophylaxis of diseases, wherein said diseases are those related to protein kinase (such as ALK) activity, such as abnormal cell proliferation, wherein the abnormal cell proliferation includes cancer.

In some embodiments, the present invention also provides a use of a pharmaceutically acceptable acid salt of a compound of formula I, or a pharmaceutical composition thereof for the manufacture of a medicament for the treatment and/or prophylaxis of diseases mediated by ALK, said diseases mediated by ALK include, but are not limited to, ALK-positive non-small cell lung carcinoma, anaplastic large cell lymphoma, inflammatory myofibroblastic tumor, nasopharyngeal carcinoma, breast cancer, colorectal cancer, diffuse large B-cell lymphoma, systemic histiocytosis, and neuroblastoma, and the like, ALK-positive non-small cell lung carcinoma is preferable.

Furthermore, the present application also provides a method for the treatment and/or prophylaxis of mammalian (such as human) diseases, wherein said diseases are those related to protein kinase (such as ALK) activity, the method comprises administering to a mammal (such as human) a therapeutically effective amount of a pharmaceutically acceptable acid salt of a compound of formula I, or a pharmaceutical composition thereof. The preferred protein kinase is ALK.

Additionally, the protein kinases comprise mutated kinases, wherein the mutated kinases are selected from mutated ALK kinase.

In some embodiments, the present application also provides a method for the treatment and/or prophylaxis of mammalian (such as human) diseases, wherein the diseases are those related to ALK activity, the method comprises administering to a mammal (such as human) a therapeutically effective amount of the pharmaceutically acceptable acid salt of the compound of formula I, or the pharmaceutical composition thereof. Diseases related to ALK activity include, but are not limited to, ALK-positive non-small cell lung carcinoma, anaplastic large cell lymphoma, inflammatory myofibroblastic tumor, nasopharyngeal carcinoma, breast cancer, colorectal cancer, diffuse large B-cell lymphoma, systemic histiocytosis, and neuroblastoma, and the like, preferably include ALK-positive non-small cell lung carcinoma.

Furthermore, the present application also provides a pharmaceutically acceptable acid salt of a compound of formula I, or a pharmaceutical composition thereof for use in a method for modulating protein kinase activity or for use in a method for the treatment and/or prophylaxis of mammalian (such as human) diseases associated with protein kinase activity. The preferred protein kinase is ALK. The protein kinases comprise mutated kinases, wherein the mutated kinases are selected from mutated ALK kinase.

In some embodiments, the present application also provides the pharmaceutically acceptable acid salt of the compound of formula I, or the pharmaceutical composition thereof for use in a method for modulating ALK activity or for use in a method for the treatment and/or prophylaxis of mammalian (such as human) diseases associated with ALK activity. Diseases related to ALK activity include, but are not limited to, ALK-positive non-small cell lung carcinoma, anaplastic large cell lymphoma, inflammatory myofibroblastic tumor, nasopharyngeal carcinoma, breast cancer, colorectal cancer, diffuse large B-cell lymphoma, systemic histiocytosis, and neuroblastoma, and the like, preferably include ALK-positive non-small cell lung carcinoma.

EXAMPLE

The purpose of following specific examples is to facilitate those skilled in the art to more clearly understand and implement the invention. They should not be construed as limiting the scope of the invention, and they are merely exemplary illustrations and typical representatives of the invention. All operations involving easily oxidized or easily hydrolyzed raw materials are carried out under a nitrogen atmosphere. Unless otherwise indicated, raw materials used in the invention are commercially available and used without further purification.

Example 1

The Preparation of the Compound of Formula I

Preparation of Intermediate 1

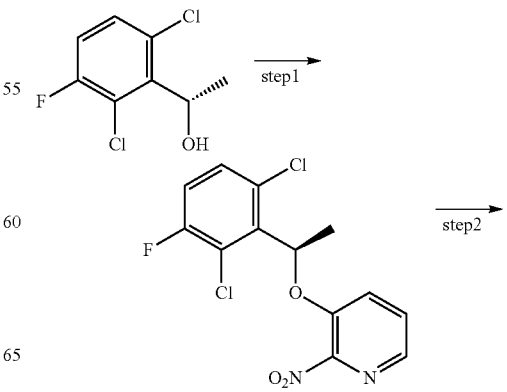

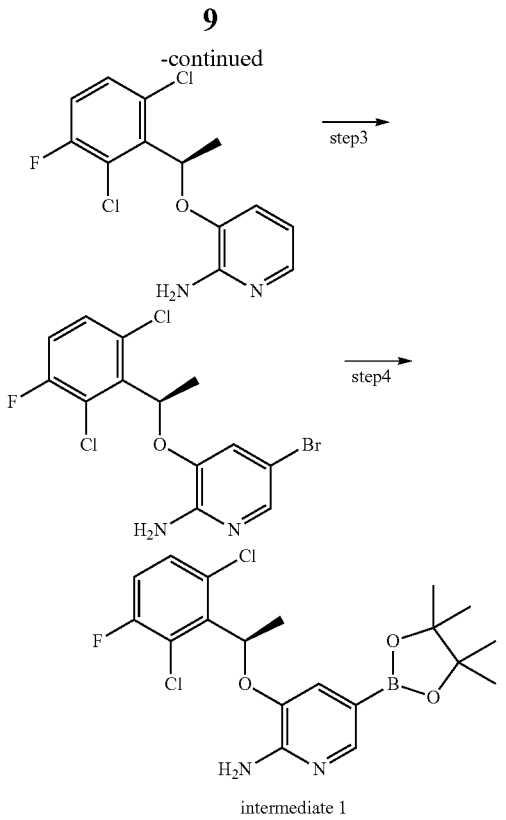

intermediate 1

Step 1: (S)-1-(2,6-dichloro-3-fluorophenyl)ethanol (20.9 g, 0.10 mol) was dissolved in anhydrous tetrahydrofuran (200 mL), and then 3-hydroxy-2-nitropyridine (16.0 g, 0.11 mol) and triphenylphosphine (40.0 g, 0.15 mol) were subsequently added under a nitrogen atmosphere. The reaction mixture was stirred at room temperature for 1 hour, cooled to 0° C., diisopropyl azodicarboxylate (40 mL, 0.15 mol) was added and the mixture was stirred for 12 hours at 0° C. After evaporating the solvent, the resulting oil product was purified by silica gel column chromatography to give (R)-3-(1-(2,6-dichloro-3-fluorophenyl)ethoxyl)-2-nitropyridine (20.2 g, 61% yield).

Step 2: To a solution of (R)-3-(1-(2,6-dichloro-3-fluorophenyl)ethoxyl)-2-nitropyridine (20.0 g, 60 mmol) in ethanol (300 mL), 2M HCl (15 mL) and reduced iron powder (27 g, 480 mmol) were added under stirring at 0° C. Upon completion of the addition, the reaction was heated under reflux for 12 hours, cooled to room temperature, filtered, the filtrate was concentrated to give (R)-3-(1-(2,6-dichloro-3-fluorophenyl)ethoxyl)-2-aminopyridine (17.0 g, 94% yield), which was directly used in the next step. MS m/z [ESI]: 301.0 [1 M+1].

Step 3:
To a solution of (R)-3-(1-(2,6-dichloro-3-fluorophenyl)ethoxyl)-2-aminopyridine (15.0 g, 50 mmol) in acetonitrile (200 mL), N-bromobutanimide (10 g, 56 mmol) was added in portions under stirring at 0° C. Upon completion of the addition, the mixture was stirred at 0° C. for 1 hour, after evaporating the solvent, dichloromethane was added, the organic phase was washed by saturated aqueous sodium bicarbonate solution, dried by anhydrous sodium sulfate, concentrated under reduced pressure, then the residue was purified by silica gel column chromatography to give (R)-3-(1-(2,6-dichloro-3-fluorophenyl)ethoxyl)-5-bromo-2-aminopyridine (9.88 g, 52% yield). MS m/z [ESI]: 380.9 [M+1].

Step 4: (R)-3-(1-(2,6-dichloro-3-fluorophenyl)ethoxyl)-5-bromo-2-aminopyridine (7.6 g, 20 mol), bis(pinacolato) diboron (7.56 g, 30 mmol), Pd(dppf)Cl$_2$(732 mg, 1 mmol), and anhydrous potassium acetate (4.90 g, 50 mmol) were added to dry dioxane (200 mL), purged with nitrogen, the mixture was stirred at 100° C. for 4 hours. After cooling, the mixture was evaporated under reduced pressure to remove the solvent, then the resulting residue was purified by silica gel column chromatography to give (R)-3-(1-(2,6-dichloro-3-fluorophenyl)ethoxyl)-5-(4,4,5,5-tetramethyl-1,3,2-dioxaborolan-2-yl)-2-aminopyridine (5.46 g, 64% yield).MS m/z [ESI]: 427.1 [M+1].

Preparation of Intermediate 2

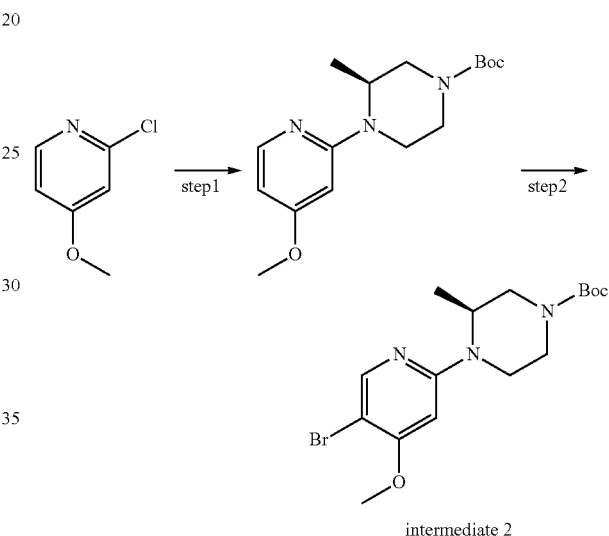

intermediate 2

Step 1:
2-Chloro-4-methoxylpyridine (2.58 g, 18 mmol), (S)-3-methyl-1-t-butoxy carbonyl-piperazine (5.4 g, 27 mmol), Pd$_2$(dba)$_3$(824 mg, 0.9 mmol), BINAP (1.12 g, 1.8 mmol), and potassium t-butoxide (5.01 g, 45 mmol) were added into dry toluene (200 mL), the reaction mixture was refluxed for 16 hours under a nitrogen atmosphere. Subsequently, the reaction mixture was cooled to room temperature, filtered, concentrated under reduced pressure, and the residue was purified by silica gel column chromatography to give the target compound, yield: 50%. MS m/z [ESI]: 308.2 [M+1].

Step 2:
To a solution of tert-butyl (S)-4-(4-methoxylpyridin-2-yl)-3-methylpiperazine-1-carboxylate (2.46 g, 8 mmol) in acetonitrile (50 mL), N-bromobutanimide(1.57 g, 8.8 mmol) was added in portions under stirring at 0° C. Upon completion of the addition, the mixture was reacted at room temperature for 2 hours, evaporated under reduced pressure to remove the solvent, after the addition of dichloromethane, the organic phase was washed by saturated aqueous sodium bicarbonate solution, dried by anhydrous sodium sulfate, concentrated under reduced pressure, then the residue was purified by silica gel column chromatography to give intermediate 2, yield: 75%. MS m/z [ESI]: 386.1 [M+1].

Preparation of the Compound of Formula I

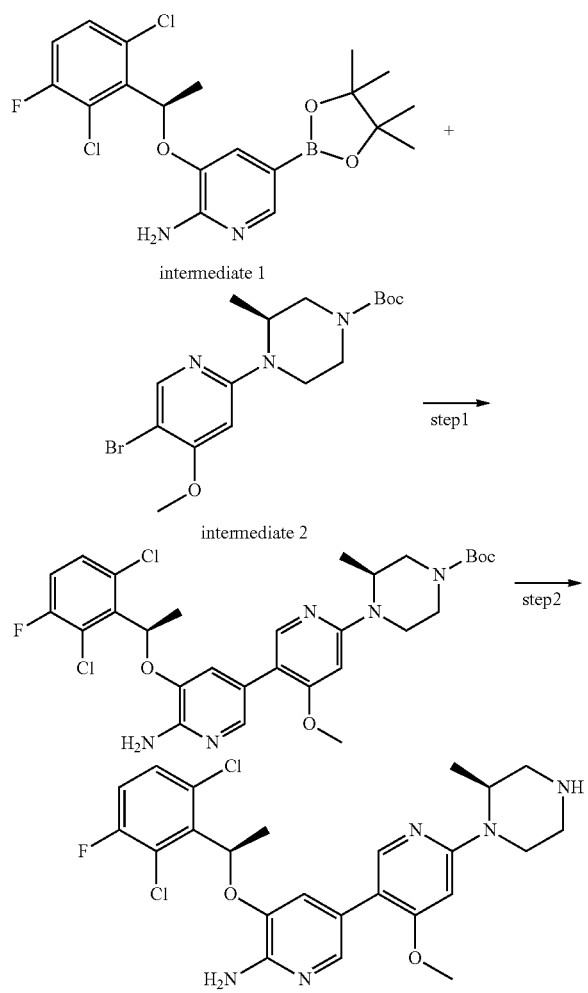

Step 1:

tert-butyl (S)-4-(5-bromo-4-methoxylpyridin -2-yl)-3-methylpiperazine -1-carboxylate (106 mg, 0.275 mmol), (R)-3-(1-(2,6-dichloro-3-fluorophenyl)ethoxyl)-5-(4,4,5,5-tetramethyl-1,3,2-dioxaborolan-2-yl)-2-aminopyridine (140 mg, 0.33 mmol), tetrakis (triphenylphosphine) palladium (32 mg, 0.0275 mmol) and cesium carbonate (179 mg, 0.55 mmol) were added in dry dioxane (10 mL) and water (1.5 mL), purged with nitrogen. The mixture was reacted at 100° C. overnight. After cooling, the resulting mixture was purified by silica gel column chromatography to give 5-((R)-1-(2,6-dichloro-3-fluorophenyl) ethoxyl)-4'-methoxy-6 '-((S)-2-methyl-4-tert-butoxycarbonyl-piperazin-1-yl)-3,3'-bipyridin-6-amine (70 mg), yield: 42%. MS m/z [ESI]: 606.2 [M+1].

Step 2:

To a solution of 5-((R)-1-(2,6-dichloro-3-fluorophenyl) ethoxyl)-4'-methoxy-6'-((S)-2-methyl-4-tert-butoxycarbonyl-piperazin-1-yl)-3,3'-bipyridin-6-amine (67 mg, 0.11 mmol) in dichloromethane (10 mL) was added trifluoroacetate (1 mL) under stirring at room temperature, the mixture was stirred for 1 hour. Aqueous sodium hydroxide solution (10 mol/L) was added to adjust the pH to more than 13, and then extracted by dichloromethane. The organic phase was dried by anhydrous sodium sulfate, filtered, concentrated, and purified by silica gel column chromatography (dichloromethane:methanol=8:1 as eluant) to give 5-((R)-1-(2,6-dichloro-3-fluoro phenyl)ethoxyl)-4'-methoxy-6'((S)-2-methylpiperazin-1-yl)-[3,3'-bipyridin]-6-amine (30 mg), yield: 55%.

MS m/z [ESI]: 506.1 [M+1];

$^1$H-NMR (400 MHz, CDCl3): δ=7.94 (1H, s), 7.71 (1H, s), 7.28-7.32 (1H, m), 7.07 (1H, t, J=8.4 Hz), 6.97 (1H, s), 6.04-6.13 (2H, m), 4.86 (2H, s), 4.57-4.59 (1H, m), 4.03 (1H, d, J=14 Hz), 3.76 (3H, s), 3.07-3.33 (4H, m), 2.88-3.00 (1H, m), 1.84 (3H, d, J=6.8 Hz), 1.34 (3H, d, J=6.8 Hz).

Example 2

The Preparation of a Pharmaceutically Acceptable Acid Salt of a Compound of Formula I 1. Preparation of Citrate Salt of a Compound of Formula I To a solution of a compound of formula I (0.01 mol) in ethanol was added citric acid-ethanol solution (10 ml, 1.2 mol/L) under stirring at room temperature. The mixture was reacted for 1 hour, then condensed to dry under reduced pressure to give off-white solid, which is identified as amorphous form by X-ray powder diffraction, mp: 225.3-226.8° C.

2. Preparation of Citrate Salt of a Compound of Formula I

To a solution of a compound of formula I (0.01 mol) in acetone was added citric acid-acetone solution (10 ml, 1.2 mol/L) under stirring at room temperature. The mixture was reacted for 1 hour, then condensed to dry under reduced pressure to give solid, which is identified as amorphous form by X-ray powder diffraction.

3. Preparation of Citrate Salt of a Compound of Formula I

To a solution of a compound of formula I (0.01 mol) in ethyl acetate was added citric acid -acetone solution (10 ml, 1.2 mol/L) under stirring at 20° C. The mixture was reacted for 1 hour, condensed to dry under reduced pressure to give solid, which is identified as amorphous form by X-ray powder diffraction.

4. Preparation of Citrate Salt of a Compound of Formula I

To a solution of a compound of formula I (0.01 mol) in 1,4-dioxane was added citric acid -acetone solution (10 ml, 1.2mol/L) under stirring at 20° C. The mixture was reacted for 1 hour, then condensed to dry under reduced pressure to give solid, which is identified as amorphous form by X-ray powder diffraction.

5. Preparation of Hydrochloride Salt of a Compound of Formula I

To a solution of a compound of formula I (0.01 mol) in ethanol was added 5 ml hydrochloric acid-ethanol solution (10%, w/w)under stirring at room temperature. The mixture was reacted for 1 hour, then the solid was precipitated, and filtered. The filter cake was dried in vacuum to give off-white solid, mp: 179.6-179.8° C.

6. Preparation of Sulfate Salt of a Compound of Formula I

To a solution of a compound of formula I (0.01 mol) in ethanol was added sulfuric acid-ethanol solution (10 ml, 1.2 mol/L) under stirring at room temperature. The mixture was reacted for 1 hour, then the solid was precipitated, and filtered. The filter cake was dried in vacuum to give pale yellow solid, mp: 186.5-189.4° C.

7. Preparation of Malate Salt of a Compound of Formula I

To a solution of a compound of formula I (0.01 mol) in ethanol was added malic acid -1,4-dioxane solution (10 ml, 1.2 mol/L) under stirring at room temperature. The mixture was reacted for 1 hour, then the solid was precipitated, and filtered. The filter cake was dried in vacuum to give off-white solid, mp: 190.4-191° C.

8. Preparation of Maleate Salt of a Compound of Formula I

To a solution of a compound of formula I (0.01 mol) in ethanol was added maleic acid -ethyl acetate solution (10 ml, 1.2 mol/L) under stirring at room temperature. The mixture was reacted for 1 hour, then the solid was precipitated, and filtered. The filter cake was dried in vacuum to give off-white solid, mp: 179.9-180.1° C.

9. Preparation of Tartrate Salt of a Compound of Formula I

To a solution of a compound of formula I (0.01 mol) in ethanol was added tartaric acid -acetone solution (10 ml, 1.2 mol/L) under stirring at room temperature. The mixture was reacted for 1 hour, then the solid was precipitated, and filtered. The filter cake was dried in vacuum to give off-white solid, mp: 225.8-226.0° C.

10. Preparation of Fumarate Salt of a Compound of Formula I

To a solution of a compound of formula I (0.01 mol) in ethanol was added fumaric acid-ethanol solution (10 ml, 1.2 mol/L) under stirring at room temperature. The mixture was reacted for 1 hour, then the solid was precipitated, and filtered. The filter cake was dried in vacuum to give off-white solid, mp: 185.3-187.7° C.

Example 3

Pharmacology Experiment

The inhibitory activity of a compound of formula I against ALK kinase and mutated ALK kinase was determined, and the therapeutic effect on human non-small cell lung carcinoma NCI-H2228 xenografts was assayed in nude mice by the following tests. It can be understood that a pharmaceutically acceptable acid salt of a compound of formula I (e.g. hydrochloride, sulfate, citrate, malate, maleate, tartrate, fumarate) has the same pharmacological activity in vivo as a compound of formula I.

1. ALK Kinase Inhibition Activity Assay

The following method was used to determine ALK kinase inhibitory activity of a compound of formula I of the present application. The inhibitory activity was indicated by $IC_{50}$, which means the concentration of the compound when ALK kinase activity was inhibited by 50%. The present application established and optimized ALK (purchased from Millipore) kinase activity assay platform using the method of homogeneous time-resolved fluorescence (HTRF, Cisbio) for measuring the activity of the compound.

Materials and Methods:
Materials:
a. White 384 Orifice plate (Perkin Elmer, Catalog No. 607290/99)
b. HEPES buffer: 50 ml of 0.05M HEPES buffer was formulated with 1M HEPES buffer (Invitrogen, Catalog No. 15630-080), by taking 2.5 ml of 1 M HEPES buffer, adding appropriate amount of distilled water ($ddH_2O$), adjusting pH to 7.0 with NaOH, and finally adding $ddH_2O$ (double distilled water) to 50 ml.
c. ALK kinase (Millipore).
d. 0.1M $Na_3VO_4$
e. 1 M $MgCl_2$
f. 0.2 M DTT
g. 10% BAS
h. DMSO
i. $ddH_2O$
j. Test compound: Compound of formula I The test was carried out according to the following procedure:
1. Preparing ALK enzyme reaction buffer: 50 mM HEPES (pH=7.0), 0.1 mM $Na_3VO_4$, 0.01% BAS, 5 mM $MgCl_2$, 1 mM DTT, placing on ice for use;
2. Using 100% DMSO to make a 3-fold serial dilution of the compound from 1 mM, adding 4 µl of each concentration to 96 µl of reaction buffer, then taking 2.5 µl and adding it to 384 well plate (OptiPlate-384, PerkinElmer), followed by adding 5 µl of kinase, uniformly mixed by centrifugation, then adding 2.5 µl of the mixed liquid of ATP and TK peptide (ATP final concentration is Km value) to initiate the reaction;
3. Placing the 384 well plate in an incubator at 23° C. for 120 minutes;
4. Adding 5 µl of TK Antibody- antibody, 5 µl of streptavidin-labeled XL-665 to stop the reaction;
5. Incubating in the incubator (22-23° C.) for 1 hour;
6. Using a microplate reader Envision (PerkinElmer) to read the fluorescent signal of the reaction: 320 nm excitation, reading 665 nm wavelength emission spectra;
7. Generating $IC_{50}$ of the compound against ALK: calculating $IC_{50}$ of the compound using GraFit6.

$IC_{50}$ of compound of formula I tested by the above method was 1.96 nM, which indicated that the compound of formula I have high ALK inhibitory activity.

2. Mutated ALK kinase Inhibition Activity Assay

Table 1 lists inhibitory activities of the compound of formula I against mutated ALK kinase. L1196M and G1269S mutated ALK kinases herein can be obtained from commercial sources.

TABLE 1

Inhibitory activities of a compound of formula I against mutated ALK kinases

| Test compound | Inhibitory activities against mutated ALK kinases $IC_{50}$ (nM) | |
| --- | --- | --- |
| | L1196M | G1269S |
| compound of formula I | 35.1 ± 5.3 | 61.3 ± 7.9 |

3. Therapeutic Effect On Human Non-Small Cell Lung Carcinoma NCI-112228 xenografts in nude mice assay The following experimental method was used: Nude mice was inoculated subcutaneously with human non-small cell lung carcinoma NCI-H2228 cells, the mice were randomly grouped (D0) and administered until the tumor grew to 80-200 $mm^3$. Administration dose and administration regimen were listed in Table 2. Measuring the tumor volume, weighing the mice, and recording the data twice a week. Tumor volume (V) was calculated as:

$V=½=a=b^2$, wherein a and b represented length and width respectively.

$T/C(\%)=(T-T_0)/(C-C_0)\times100$, wherein T, C respectively represented the tumor volume at the end of the experiment; $T_0$, $C_0$ respectively represented the tumor volume at the start of the experiment.

When tumor regression was observed, $T/C(\%)=(T-T_0)/T_0\times100$, wherein T was the tumor volume at the end of the experiment; $T_0$ was the tumor volume at the start of the experiment.

Inhibition rate(%)=100-T/C(%), partial regression indicated that the tumor diminished but didn't disappear, complete regression indicated that the tumor disappeared.

TABLE 2 therapeutic effect of compound of formula I on human non-small cell lung carcinoma NCI-H2228 xenografts in nude mice

| Group | Administration | Route | Average tumor volume (mm³) D0 | SD | Average tumor volume (mm³) D21 | SD | % T/C D21 | % Inhibition rate D21 | P values D21 | Partial Regression (n) | Complete Regression (n) | The number of animals per group |
|---|---|---|---|---|---|---|---|---|---|---|---|---|
| Solvent | D0-20 | PO | 139.6 | ±11.5 | 1319.8 | ±322.6 | — | — | — | 0 | 0 | 12 |
| compound of formula I 12.5 mg/kg | D0-13 | PO | 134.3 | ±14.8 | 394.8 | ±315.6 | 22 | 78 | 0.000 | 1 | 0 | 6 |
| compound of formula I 25 mg/kg | D0-13 | PO | 131.0 | ±7.2 | 21.7 | ±35.4 | −83 | 183 | 0.000 | 2 | 4 | 6 |

In the table: the solvent group (distilled water containing 0.1% Tween-80) was a control group, the compound of the treatment groups was formulated with distilled water containing 0.1% Tween-80.

D0-20 represented administrating once a day from day 0 (D0) for consecutive 21 days; D0-13 represented administrating once a day from day 0 (D0) for consecutive 14 days.

P value was obtained from student's t test compared with the control group.

n was the number of mice, for the control group, the number of test mice n was 12, and n was 6 for the treatment group.

The invention claimed is:

1. A pharmaceutically acceptable acid salt of a compound of formula I, wherein the compound of formula I has the following structure:

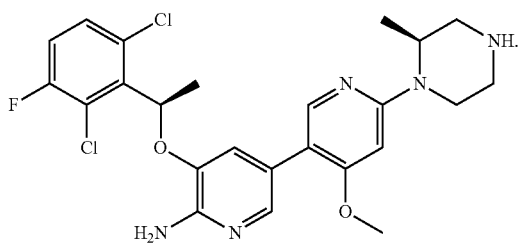

formula I

2. The pharmaceutically acceptable acid salt of the compound of formula I according to claim 1, wherein the pharmaceutically acceptable acid includes inorganic and organic acids.

3. The pharmaceutically acceptable acid salt of the compound of formula I according to claim 1, wherein the pharmaceutically acceptable acid is selected from sulfuric acid, carbonic acid, nitric acid, hydrochloric acid, hydrobromic acid, hydroiodic acid, phosphoric acid, metaphosphoric acid, trifluoroacetic acid, lactic acid, fumaric acid, mandelic acid, glycolic acid, p-toluenesulfonic acid, o-toluenesulfonic acid, citric acid, methanesulfonic acid, formic acid, acetic acid, benzoic acid, phenylacetic acid, malonic acid, cinnamic acid, malic acid, maleic acid, tartaric acid, oxalic acid, acrylic acid, crotonic acid, oleic acid, and linoleic acid.

4. The pharmaceutically acceptable acid salt of the compound of formula I according to claim 1, which is selected from the group consisting of:

5-((R)-1-(2,6-dichloro-3-fluorophenyl)ethoxy)-4'-methoxy-6'-((S)-2-methylpiperazin-1-yl)-3,3'-bipyridin-6-amine hydrochloride, 5-((R)-1-(2,6-dichloro-3-fluorophenyl)ethoxy)-4'-methoxy-6'-((S)-2-methylpiperazin-1-yl)-3,3'-bipyridin-6-amine sulfate, 5-((R)-1-(2,6-dichloro-3-fluorophenyl)ethoxy)-4'-methoxy-6'-((S)-2-methylpiperazin-1-yl)-3,3'-bipyridin-6-amine citrate, 5-((R)-1-(2,6-dichloro-3-fluorophenyl)ethoxy)-4'-methoxy-6'-((S)-2-methylpiperazin-1-yl)-3,3'-bipyridin-6-amine malate, 5-((R)-1-(2,6-dichloro-3-fluorophenyl)ethoxy)-4'-methoxy-6'-((S)-2-methylpiperazin-1-yl)-3,3'-bipyridin-6-amine maleate, 5-((R)-1-(2,6-dichloro-3-fluorophenyl)ethoxy)-4'-methoxy-6'-((S)-2-methylpiperazin-1-yl)-3,3'-bipyridin-6-amine tartrate, and 5-((R)-1-(2,6-dichloro-3-fluorophenyl)ethoxy)-4'-methoxy-6'-((S)-2-methylpiperazin-1-yl)-3,3'-bipyridin-6-amine fumarate.

5. A citric acid salt of a compound of formula I, wherein the compound of formula I has the following structure:

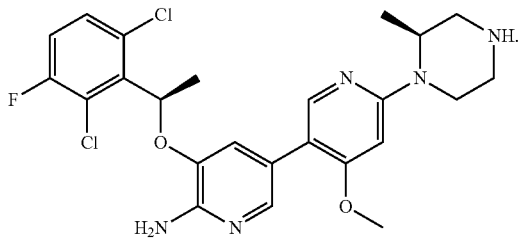

formula I

6. The salt of claim 5, wherein a molar ratio of the compound of formula I to the citric acid is 1:0.5, 1:1, 1:1.5, 1:2, 1:2.5, 1:3, 1:3.5 or 1:4.

7. The salt of claim 5, wherein a molar ratio of the compound of formula I to the citric acid is 1:1.

8. A pharmaceutical composition comprising a therapeutically effective amount of the pharmaceutically acceptable acid salt of the compound of formula I according to claim 1, and a pharmaceutically acceptable carrier, excipient or diluents.

9. A pharmaceutical composition comprising a therapeutically effective amount of a citric acid salt of a compound of formula I, and a pharmaceutically acceptable carrier, excipient or diluents, wherein the compound of formula I has the following structure:

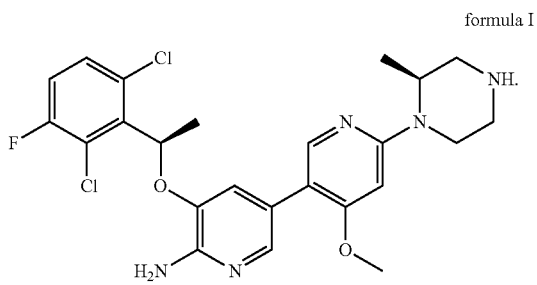 [SMILES: COc1cc(N2CCNC[C@@H]2C)ncc1-c1cnc(N)c(O[C@H](C)c2c(Cl)ccc(F)c2Cl)c1]

formula I

10. The pharmaceutical composition of claim 9, wherein a molar ratio of the compound of formula I to the citric acid is 1:0.5, 1:1, 1:1.5, 1:2, 1:2.5, 1:3, 1:3.5 or 1:4.

11. A method for preparing the pharmaceutically acceptable acid salt of the compound of formula I according to claim 1, which comprises reacting the compound of formula I with the pharmaceutically acceptable acid.

12. The method according to claim 11, wherein the pharmaceutically acceptable acid is selected from sulfuric acid, carbonic acid, nitric acid, hydrochloric acid, hydrobromic acid, hydroiodic acid, phosphoric acid, metaphosphoric acid, trifluoroacetic acid, lactic acid, fumaric acid, mandelic acid, glycolic acid, p-toluenesulfonic acid, o-toluenesulfonic acid, citric acid, methanesulfonic acid, formic acid, acetic acid, benzoic acid, phenylacetic acid, malonic acid, cinnamic acid, malic acid, maleic acid, tartaric acid, oxalic acid, acrylic acid, crotonic acid, oleic acid, and linoleic acid.

13. The method according to claim 11, wherein the salt is prepared by the reaction of the compound of formula I dissolved in a single solvent or mixed solvents containing the corresponding pharmaceutically acceptable acid, or the salt is prepared by the reaction of the compound of formula I dissolved in a single solvent or mixed solvents followed by adding a corresponding acid.

14. The method according to claim 11, wherein the molar ratio of the compound of formula I to the pharmaceutically acceptable acid is 1:0.5-4.

15. The method according to claim 11, wherein the reaction temperature is 0° C. to the boiling point of the solvent system.

16. The method according to claim 11, wherein the reaction is carried out under an inert gas.

17. The method according to claim 11, wherein the reaction time is 0.5-5 h.

18. The method according to claim 13, wherein the solvent is selected from tetrahydrofuran, dioxane, diisopropyl ether, diethyl ether, methanol, ethanol, isopropanol, acetone, acetonitrile, ethyl acetate, ethyl formate, hexane, methylene chloride, chloroform, and any combination thereof.

19. A method for the treatment of a disease mediated by ALK, wherein the method comprises administering to a mammal in need thereof, the pharmaceutically acceptable acid salt of the compound of formula I according to claim 1, wherein the disease mediated by ALK is ALK-positive non-small cell lung carcinoma, anaplastic large cell lymphoma, inflammatory myofibroblastic tumor, nasopharyngeal carcinoma, breast cancer, colorectal cancer, diffuse large B-cell lymphoma, systemic histiocytosis, or neuroblastoma.

20. A method for the treatment of a disease mediated by ALK, wherein the method comprises administering to a mammal in need thereof, the pharmaceutical composition according to claim 8, wherein the disease mediated by ALK is ALK-positive non-small cell lung carcinoma, anaplastic large cell lymphoma, inflammatory myofibroblastic tumor, diffuse large B-cell lymphoma, or neuroblastoma.

* * * * *